(12) United States Patent
Lind et al.

(10) Patent No.: US 8,403,920 B2
(45) Date of Patent: Mar. 26, 2013

(54) LASER TRABECULECTOMY WITH ENERGY DISSIPATING INJECTION

(75) Inventors: Casey Jean Lind, Orange, CA (US); Robert Joseph Sanchez, Jr., Oceanside, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 182 days.

(21) Appl. No.: 12/957,847

(22) Filed: Dec. 1, 2010

(65) Prior Publication Data

US 2012/0143052 A1  Jun. 7, 2012

(51) Int. Cl.
*A61F 9/008* (2006.01)

(52) U.S. Cl. .............................. 606/6; 606/4
(58) Field of Classification Search .................. 606/4, 6
See application file for complete search history.

(56) References Cited

U.S. PATENT DOCUMENTS

| | | | |
|---|---|---|---|
| 4,865,029 A * | 9/1989 | Pankratov et al. ................ 606/4 |
| 5,431,646 A | 7/1995 | Vassiliadis et al. |
| 5,865,831 A | 2/1999 | Cozean et al. |
| 6,142,990 A | 11/2000 | Burk |
| 6,241,721 B1 | 6/2001 | Cozean et al. |
| 7,564,946 B2 * | 7/2009 | Gertner ........................... 378/65 |
| 2002/0013572 A1 * | 1/2002 | Berlin .............................. 606/4 |
| 2005/0277864 A1 * | 12/2005 | Haffner et al. .................... 604/8 |
| 2008/0228127 A1 * | 9/2008 | Burns et al. ....................... 604/9 |

* cited by examiner

Primary Examiner — Henry M Johnson, III
Assistant Examiner — John R Downey
(74) Attorney, Agent, or Firm — Kenneth Bassinger (57) ABSTRACT

A method to perform high resolution tissue ablation including the steps of forming a beam to deliver optical energy and providing an energy dissipating material is provided. The steps of selecting an area of interest in a target tissue and placing the energy dissipating material adjacent to the area of interest may be included. The steps of directing the beam to the area of interest and scanning the beam across the area of interest to ablate the target tissue may be further included. Also provided is an apparatus and a system for high resolution tissue ablation including a beam to provide optical energy and an injector for placing an energy dissipating material adjacent to an area of interest. Further, the apparatus and system may include at least a mirror and a lens for directing the beam to the area of interest and scanning the beam to ablate target tissue.

9 Claims, 10 Drawing Sheets

LASER TRABECULECTOMY WITH ENERGY DISSIPATING INJECTION

BACKGROUND

1. —Field of the Invention

The embodiments described herein relate to the field of laser-based surgical procedures for ophthalmology. More particularly, the embodiments relate to the field of laser-based surgical procedures for the treatment of glaucoma.

2. —Description of Related Art

Figure 1:
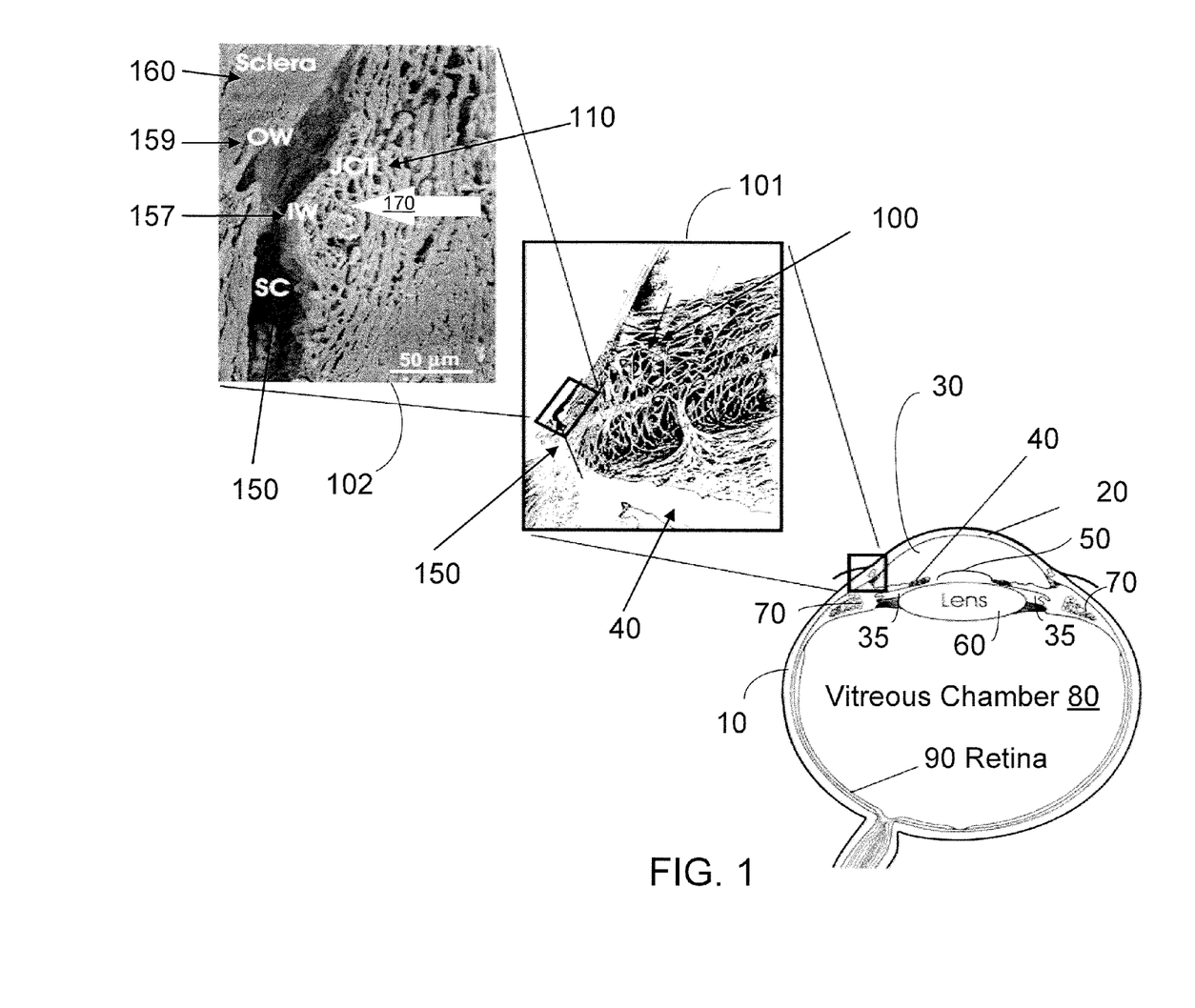
FIG. 1 shows the anatomy of the eye, including Schlemm's Canal and the Trabecular Meshwork among other parts that are of relevance to some embodiments.

Glaucoma is a disease in which the optic nerve is damaged, leading to progressive, irreversible loss of vision. An increase in intraocular pressure (IOP) is often associated with glaucoma. IOP is a function of episcleral venous pressure, the production of aqueous humor within the anterior chamber of the eye, and its outflow through the trabecular meshwork and the uveoscleral pathway. The aqueous humor is a clear liquid that primarily fills the Anterior Chamber (AC, FIG. 1, 30). The aqueous humor is produced by specialized cells in the Ciliary Body (FIG. 1, 70). Aqueous humor drains through the Trabecular Meshwork (TM. FIG. 1, 100), whose Juxtacanicular Trabecular Meshwork (JCT, FIG. 1, 110) lines Schlemm's Canal (SC, cf. FIG. 1, 150) allowing flow into the away from the AC. Schlemm's Canal (SC, cf. FIG. 1, 150) is coupled to a network of collector channels allowing the aqueous humor to be absorbed by the body as it is drained away from the eye.

There are mainly two surgical strategies to manage glaucoma and the pathologies associated with it that involve minor invasive surgery. One strategy is by affecting the generation of aqueous humor (e.g. reducing it) in the eye. The other strategy is augmenting drainage of the fluid out of the eye's cavities, through Schlemm's Canal. According to the first strategy, a method called endoscopic cyclophotocoagulation (ECP) uses a laser beam to stunt the Ciliary Body. The production of aqueous humor by the stunted cells is then reduced significantly, resulting in a lowering of IOP. ECP is a bi-manual procedure that requires endoscopic visualization to precisely target and gauge the laser action on the Ciliary Body in real time.

According to a second strategy, the TM outflow path may be bypassed. There are different ways to achieve this. Some of these techniques utilize laser ablation of the TM to gain direct access to SC and the collector channels. For example, Selective Laser Trabeculoplasty (SLT) utilizes a laser to target intracellular melanin. To perform SLT, a frequency doubled (532 nm) Q-switched Nd:YAG laser with a 400 µm spot size may be used. The laser may be operated in pulsed mode to deliver 0.4-1 mJ of energy for about 0.3 ns (nanoseconds). This may produce a biological effect on the TM, stimulating a mechanism to enhance aqueous outflow from the eye via SC. SLT protects the TM against thermal or coagulation effects by selectively targeting the pigmented cells in the eye. Thus, surrounding tissue may be preserved. However, in eyes with little pigmentation the laser may target only a limited area. Another technique of choice may be Argon Laser Trabeculoplasty (ALT). ALT consists in the opening of the drainage angle of the eye by simply piercing through the TM via tissue ablation. However, this technique may induce thermal damage to the surrounding tissue, scarring it. Once scar tissue develops surrounding the area of interest it becomes difficult to repeat the procedure in the same area, or its vicinity. Also, scar tissue may block the drainage of aqueous humor into SC.

Further within the second strategy, some approaches may include the use of a stent, or "shunt" surgically implanted in the eye via an ab-interno procedure. In some cases the implant may provide a tube or conduit that pierces through the TM, allowing aqueous humor to flow out of the eye via the SC and collector channels. However, these devices may easily bend or occlude as the area heals rendering the bypass less effective over time.

Therefore, there is a need for a minimally invasive Trabeculectomy procedure that limits tissue ablation to the Trabecular Meshwork only, causing minimal damage in the surrounding tissue.

SUMMARY

In accordance with some embodiments disclosed herein a method to perform high resolution tissue ablation may include the steps of forming a beam to provide optical energy and providing an energy dissipating material. Also, the steps of selecting an area of interest in a target tissue and placing the energy dissipating material adjacent to the area of interest, limiting the propagation of the ablative energy, may be included. The steps of directing the beam to the area of interest and scanning the beam across the area of interest to ablate the target tissue may be further included.

An apparatus to perform high resolution tissue ablation according to some embodiments disclosed herein may include a beam to provide optical energy and an injector for placing an energy dissipating material adjacent to an area of interest. Further, the apparatus may include at least a mirror and a lens for directing the beam to the area of interest and scanning the beam across the area of interest to ablate target tissue.

A system to perform high resolution tissue ablation according to some embodiments disclosed herein may include optical elements to provide a beam carrying optical energy. The beam has a fluence over an ablation threshold in an effective fluence portion of the tissue. Further, the system may include a selected area of interest in a target tissue to receive the beam; and a biocompatible, energy-dissipating material placed adjacent to the area of interest to reduce the fluence of the beam.

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

FIG. 1 shows the anatomy of the eye 10, including Schlemm's Canal (SC) 150 and Trabecular Meshwork (TM) 100, as they are of relevance to some embodiments. The eye globe 10 is composed of the Cornea 20, covering Anterior Chamber 30, which is limited in the back by Iris 40. Iris 40 creates Pupil 50 in its central opening. Pupil 50 opens the optical path to Lens 60 by stretching Iris 40 using muscles within the Ciliary Body 70 (also referred as "ciliary process"). The space behind Iris 40 and delimited by Lens 60, Ciliary Body 70, and Iris 40 is Posterior Chamber 35. Muscles in Ciliary Body 70 also stretch and change the shape of Lens 60, to project an image in Retina 90. The optical path of light rays going from Lens 60 to Retina 90 traverses Vitreous Chamber 80, filled with Vitreous Humor.

As shown in FIG. 1, there is continuity between chambers 30 and 35, which are filled with aqueous humor secreted by cells in Ciliary Body 70. Aqueous humor provides transparency for light rays entering the eye, and is a contributor to intraocular pressure (IOP) to keep optical elements in the anterior chamber properly positioned, to create the desired image on the Retina.

To relieve IOP, aqueous humor is drained out of the eye through Schlemm's Canal (SC) 150. The tissue structure surrounding the Canal lies in expanded region 101 in FIG. 1, at the angle of chamber 30 formed by the Iris 40, Ciliary Body 70, Sclera 160 (Scleral Spur), Trabecular Meshwork 100 and Cornea 20. Region 101 includes the Trabecular Meshwork (TM) 100, Iris 40, sclera spur, ciliary muscles and Schlemm's Canal (SC) 150. TM 100 is a porous tissue that filters the aqueous humor into Schlemm's Canal 150. SC 150 is lined by a layer of the TM 100 known as the Juxtacanicular Trabecular Meshwork (JCT) 110, illustrated in further expanded area 102. SC 150 provides a conduit to transport fluid out of chambers 30 and 35. A detailed view of SC 150 is shown in further expanded area 102. SC 150 has a lumen surrounded by inner wall (IW) 157 and outer wall (OW) 159. Not shown in FIG. 1 are collector channels coupling SC 150 to the venous system. Area 102 in FIG. 1 also includes Sclera 160, which includes supporting tissue giving the eye its white color. Cornea 20 is a transparent tissue continuous with Sclera 160.

Regulating the IOP is a delicate physiological process including control of the amount of aqueous humor produced by Ciliary Body 70, and the amount of aqueous humor flowing out through SC 150. Typically, in open angle glaucoma the porous tissue in TM 100 or JCT 110 may be blocked, reducing or completely blocking the outflow of aqueous humor into SC 150. According to some embodiments, energy flux 170 may be applied to JCT 110 or TM 100 (illustrated in FIG. 1) in order to ablate the blocking tissue. Thus, energy flux 170 may open up a canal through TM 100 and JCT 110, to allow flow of aqueous humor into SC 150, Region 101 and area 102 in FIG. 1 are not shown to scale, in some embodiments the portion of TM 100 that may be affected has a cross section of a few hundred microns. For example, the area of the affected portion in 102 on average is about 250 µm in width across the major diameter, as seen from the direction of energy flux 170.

The geometry of SC 150 may include variations in its luminal cross section along a direction perpendicular to the plane in FIG. 1. Also, the thickness of TM 100 and JCT 110 may vary widely in a direction perpendicular to the plane in FIG. 1. This irregular geometry may complicate the treatment of glaucoma and other malignancies associated with SC 150, TM 100, and JCT 110, presenting stringent spatial precision and control requirements.

In some embodiments consistent with FIG. 1, energy flux 170 may be provided by electromagnetic pulses, or light pulses. For example, energy flux 170 may be a laser beam emitting pulses of coherent light having a fluence that produces ablation of TM 100 or JCT 110. The fluence of a laser beam is the amount of electromagnetic energy transmitted by the beam through a certain area, integrated over time. Fluence provides a value of the amount of energy density being transmitted to the tissue. Energy density is a parameter that may determine whether or not a cell is ablated, or damaged.

In some embodiments, it is desired to ablate the tissue of TM 100 and JCT 110. This means that the fluence provided by laser beam 170 may be high enough to vaporize cells of TM 100 including their contents. In this process, water is vaporized and organic compounds burned or decomposed so that a hole is drilled through the tissue.

Figure 2:
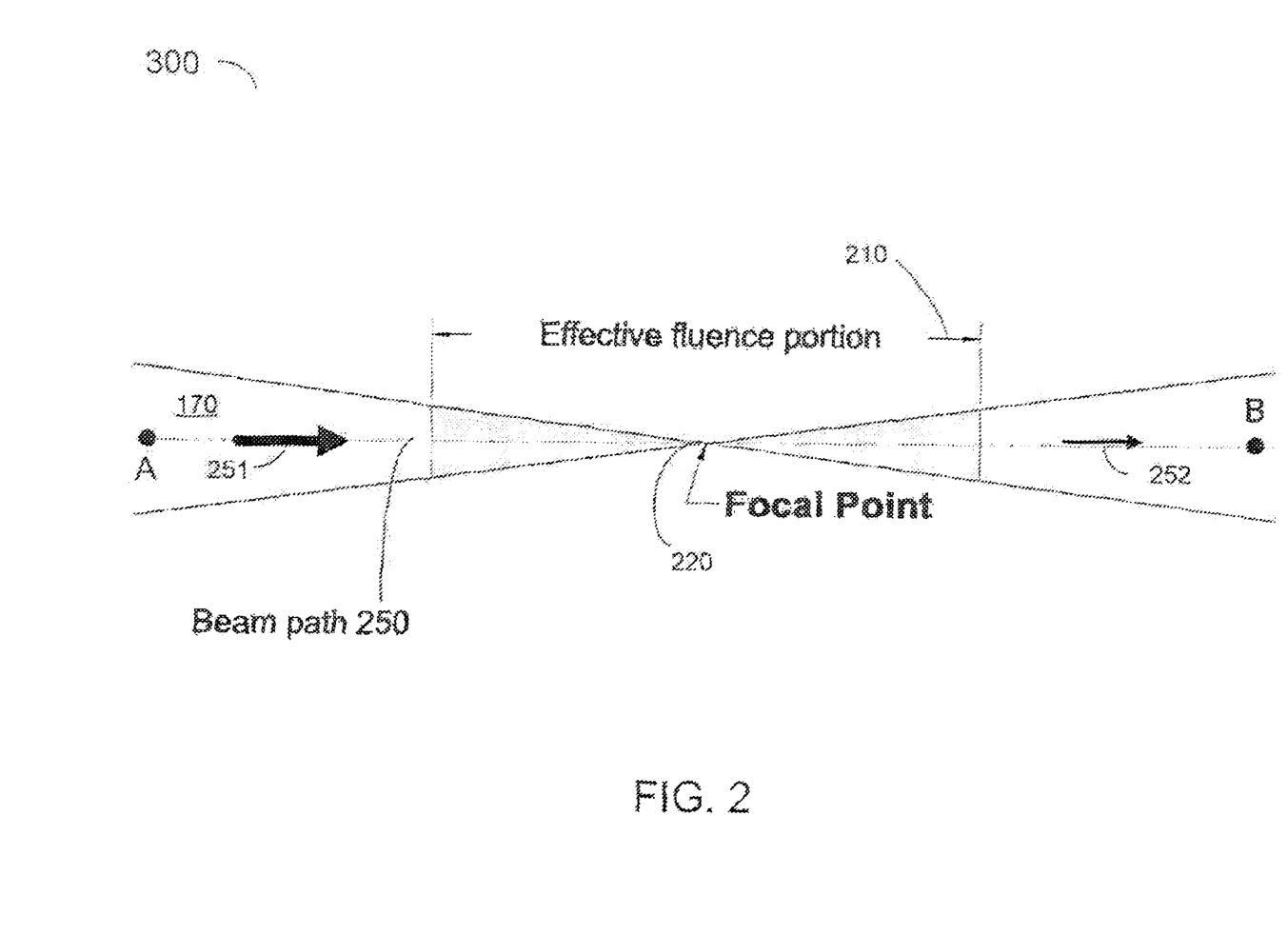
FIG. 2 shows a light beam having an input fluence converging to a focal point according to a beam path.

FIG. 2 shows light beam 170 traveling from left to right. Beam 170 has input fluence 251 converging to focal point 220 according to beam path 250 and creating effective fluence portion 210, according to some embodiments. Output fluence 252 results after beam 170 passes focal point 220. In embodiments consistent with FIG. 2, fluence 251 of beam 170 changes along beam path 250 from point A to point B. Point A may be located along a portion of the path of beam 170 before effective fluence portion 210. Point B may be located along a portion of beam path 250 after effective fluence portion 210. The change in fluence between point A and point B may be due to geometric features of beam 170. For example, the natural reduction in beam cross section as beam 170 goes into focal point 220 and the principle of conservation of energy may result in an increasing fluence for beam 170 in the portion between point A and point 220. Likewise, as the beam moves from point 220 to point B, its cross section increases, thereby reducing fluence 251 to a lower output fluence 252.

As a result of the increase and decrease of beam fluence from point A to point B, a maximum fluence may be reached at point 220. Furthermore, portion 210 of beam path 250 may be selected such that fluence 251 of beam 170 is higher than a fluence threshold value, ψ, along the entire portion. In some embodiments, ψ, may be a fluence ablation threshold for cells included in the TM 100 and the JCT 110. The fluence ablation threshold may be determined by certain physiological characteristics particular to TM 100 and JCT 110. Furthermore, the ablation threshold may also depend on the wavelength of the laser light being used in beam 170. Other characteristics of the laser beam 170 may affect the precise value of the fluence ablation threshold. If laser beam 170 is a pulsed laser beam having a repetition rate, Ω, and pulse duration, τ, the fluence ablation threshold may be dependent on Ω and τ. For example, the fluence ablation threshold may be lower for a higher repetition rate, Ω, because more laser pulses per unit time may have a cumulative effect. Also, fluence ablation threshold may be lower for a shorter pulse duration, τ, because Ω may be substantially increased with shorter pulse duration.

In the presence of a material having scattering properties and absorption properties, beam 170 may suffer loss of energy. Thus, fluence 251 may have a substantially lower value 252 close to point B than the fluence value at point A. In a scattering and absorbing medium, fluence 251 at point B may be lower than at point A for points A and B symmetrically located with respect to focus 220 along path 250.

Figure 3:
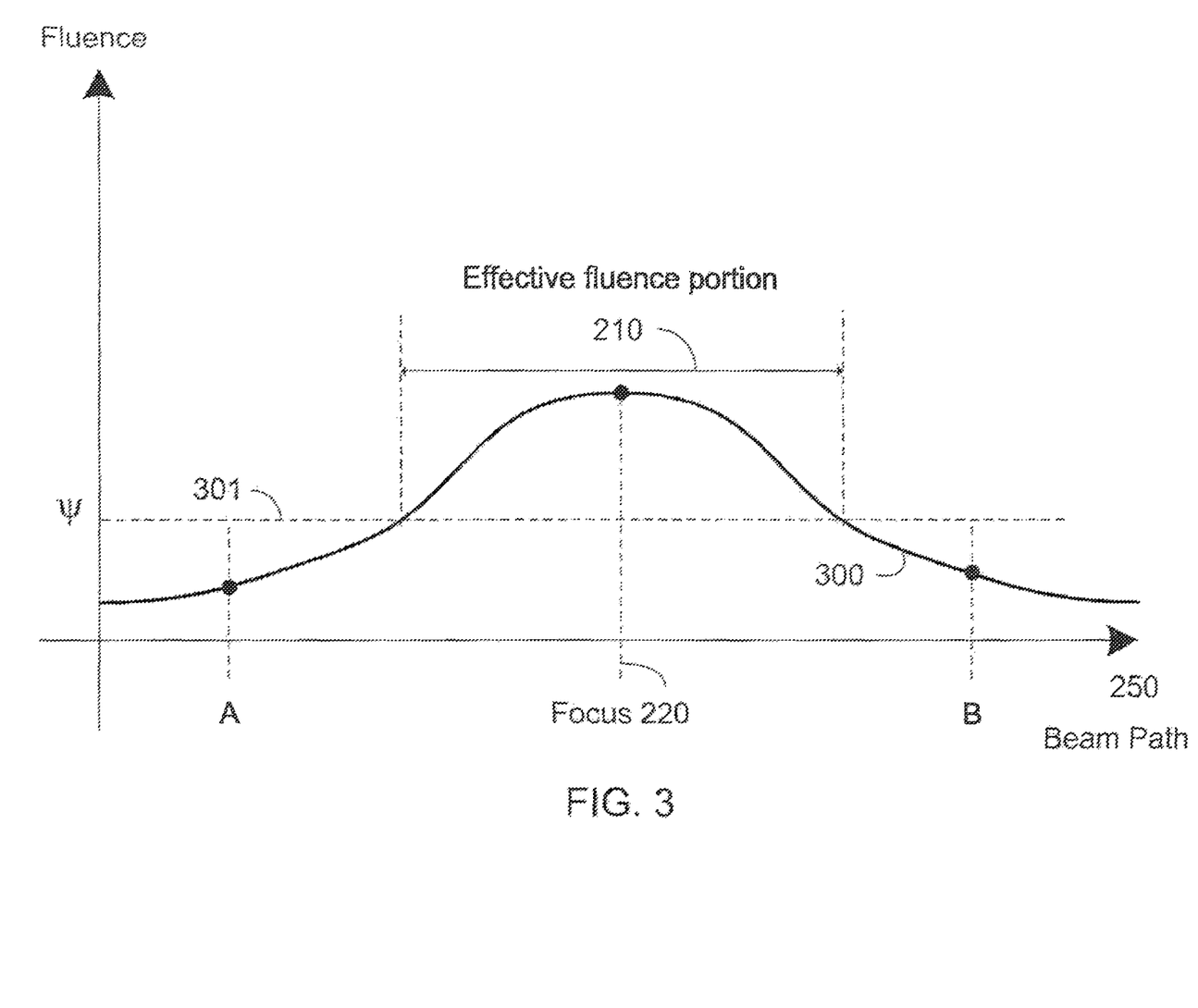
FIG. 3 shows a curve of the fluence of a laser along a beam path having a focal point, according to some embodiments.

FIG. 3 shows curve 300 for fluence 251 in beam 170 along path 250 having focal point 220, according to some embodiments. Also shown in FIG. 3 is effective fluence portion 210, where beam fluence 251 is higher than threshold, ψ, 301. If ψ 301 is a fluence ablation threshold for tissue along path 250, then cells located in portion 210 may be ablated by beam 170. Even though curve 300 illustrated in FIG. 3 is symmetric about laser focus 220, some embodiments consistent with the main features depicted in FIG. 3 may not be symmetric about laser focus 220. The exact shape of curve 300 is determined by the precise values of index of refraction and absorption, and the scattering of light at the wavelength of laser beam 170, for each point along path 250. In a heterogeneous medium such as TM 100 or JCT 110, the values for index of refraction, absorption, and scattering may vary dramatically from point to point, even for the same wavelength. The wavelength of laser beam 170 and the optical power of the device used to produce focal point 220 may also affect the length of effective fluence portion 210. As a rule of thumb, the length of portion 210 may be proportional to the wavelength of the laser beam 170 used. Also, the length of portion 210 may be inversely proportional to the numerical aperture (NA) of the optical device used to deliver laser beam 170. For example, using an Ar-ion laser (λ~488 nm) or a frequency doubled Nd:YAG laser (λ~532 nm), the length of portion 210 may be about 200 μm or more.

In the treatment of glaucoma the spatial resolution needed to target blocking portions of SC 150, TM 100 or JCT 110 may be stringent. In some situations, the resolution needed may be smaller than what can be provided by conventional lasers, optical devices, or the user's skill level. This may cause ablation through a portion 210 of tissue larger than what is required to effectively treat a malignancy. Such an outcome may be undesirable from the point of view of creating unnecessary damage to healthy tissue. It also may induce scarring in areas surrounding the damaged tissue, rendering the treatment ineffective over time.

Figure 4:
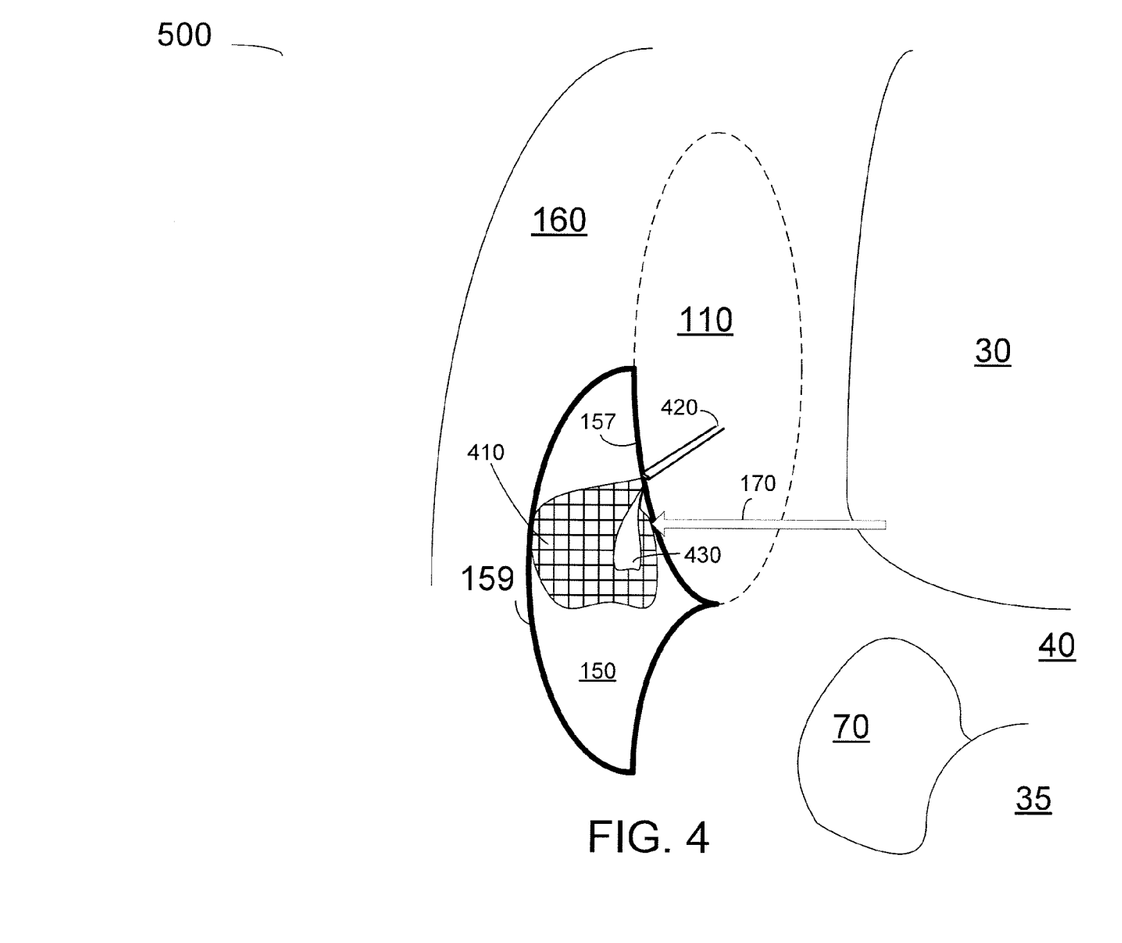
FIG. 4 shows a light beam ablation procedure in the Trabecular Meshwork in the presence of an energy-dissipating material, according to some embodiments.

FIG. 4 shows light beam ablation procedure 400 for TM 100 and JCT 110 in the presence of energy-dissipating material 410, according to some embodiments. Material 410 limits tissue ablation by beam 170 to TM 100 in a reduced portion, compared to what would be the case in the absence of material 410. Energy-dissipating material 410 is a biocompatible material that may be removed with water or may be disposed naturally by the tissue, after the procedure. An example of material 410 is a viscoelastic foam, delivered by injector 420. Viscoelastic foam 410 may be formed with a viscoelastic fluid including numerous air bubbles entrapped within it. Gas bubbles in one aspect of foam 410 come pre-encapsulated in a viscoelastic fluid. In other embodiments, injector 420 includes a dual chamber with a mixing nozzle/tip combination to inject bubbles in the fluid.

Once energy-dissipating material 410 is placed by injector 420 into SC 150, beam 170 may be used to oblate TM 100 or JCT 110, with high resolution in penetration depth and cross-section. In the absence of foam 410, portions where SC 150 may be collapsed or have a contracted lumen between IW 157 and OW 159 may be vulnerable to laser beam 170. In the presence of foam 410, laser beam 170 may not ablate tissue beyond TM 100, JCT 110, and SC 150 due to the highly localized resolution produced by the presence of the highly dissipative material 410.

Some embodiments consistent with FIG. 4 may further include colored dye 430 in foam 410. For eyes having low pigmentation (such as light colored eyes: blue, green, grey), TM 100 may be hard to visualize, thus dye 430 may help the user to target beam 170 through TM 100. For example, dye 430 may provide high contrast for TM 100 with respect to tissue background. Dye 430 may be a fluorescent material that glows upon being subjected to certain light sources such as beam 170. Furthermore, in some embodiments dye 430 may have a special affinity to TM 100 so that it adheres mostly to that tissue portion.

According to embodiments consistent with FIG. 4, viscoelastic foam 410 may press against OW 159 in SC 150. Thus, in situations where SC 150 may have a collapsed lumen, viscoelastic foam 410 may form a separation between IW 157 and OW 159. This may further ensure that beam 170 ablates only a limited area of TM 100 or JCT 110, and not IW 157 or OW 159.

Not shown in FIG. 4 is an optical system used to deliver beam 170 into TM 100 and JCT 110. Embodiments consistent with FIG. 4 may use a gonioscope including a mirror in order to direct laser beam 170 to the target area included in area 102. Furthermore, a gonioscope may offer the ability for a surgeon to image the area to be ablated onto a microscope. According to some embodiments, the target area, included in region 101 and area 102 in FIG. 1 may be as small as a few 100 micrometers in cross section. Thus, the use of a high magnification microscope may be desirable to visualize TM 100 and JCT 110 as procedure 400 progresses. Also, use of a gonioscope coupled to a microscope may enable proper manipulation of injector 420 during procedure 400.

In the composition of viscoelastic foam 410, a dual phase having gas bubbles with refraction index $n_2$ embedded in a medium with refraction index $n_1$ may provide energy dissipation. For example, the fluence of beam 170 may be suppressed due to an increased scattering power of the medium. This will be described in detail with reference to FIG. 6, below.

Figure 5:
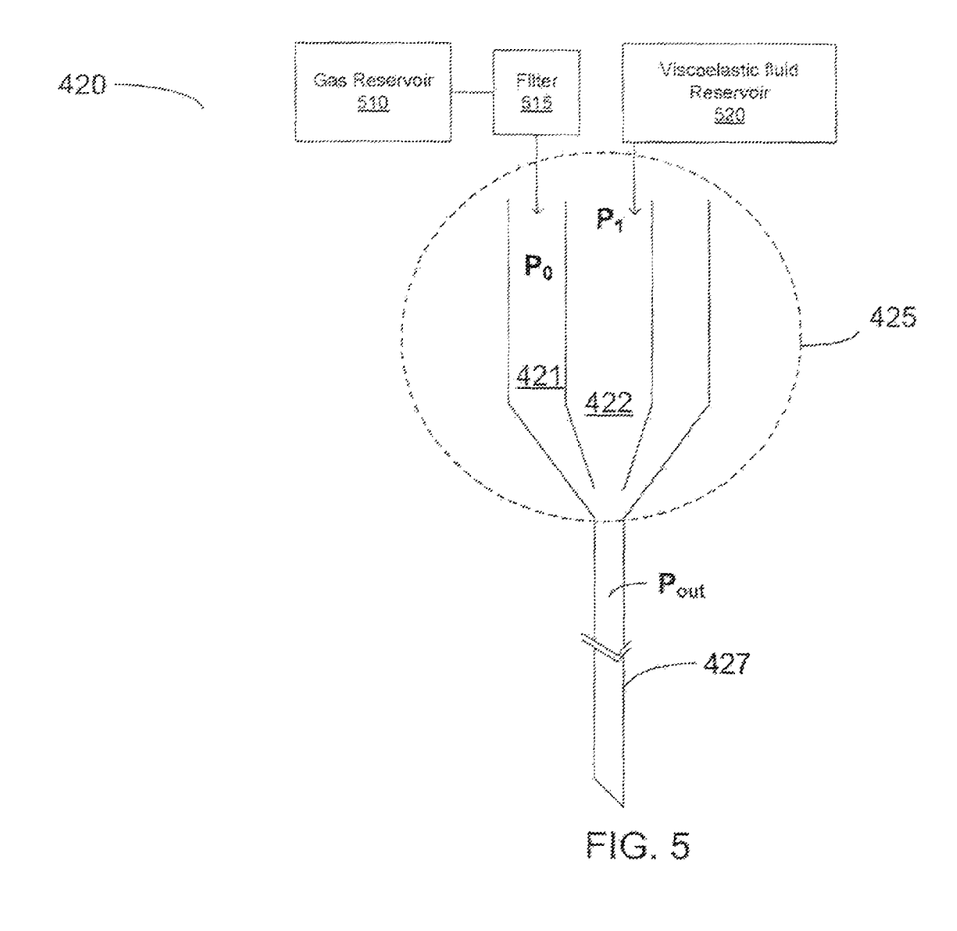
FIG. 5 shows an injector used to place an energy-dissipating material in the target tissue, according to some embodiments.

FIG. 5 shows injector 420 used to place highly energy-dissipating material 410 in the target tissue, according to some embodiments. As shown in FIG. 5, injector 420 includes nozzle 425 and delivery needle 427. Nozzle 425 has a double chamber having compartment 421 including a gas at pressure $P_0$, and compartment 422 including a viscoelastic material at pressure $P_1$. Pressure $P_{out}$ may be somewhat higher than the pressure at the target tissue where the injector is placed due to the compression of viscoelastic material along needle 427. According to some embodiments, $P_{out}$ is less than $P_0$, and $P_1$, thus creating a flux of gas and viscoelastic material through nozzle 425 at the end of compartments 421 and 422. The nozzle has the effect of increasing the flow speed, producing turbulence at its tip. Turbulent flow facilitates the mixing of gas from reservoir 510 and viscoelastic liquid in reservoir 520. The mixture over-saturates the viscoelastic liquid with gas, giving rise to bubbles, and thus the resulting material is a viscoelastic foam 410. Foam 410 flows through needle 427 which has a length that provides stabilization to the flow speed, and a reduced cross section to minimize tissue stress. In some embodiments, needle 427 has a length of several cm (2 cm or more), and a diameter of less than 500 μm. Additional features may be included in the interior portion of nozzle 425 or needle 427 to increase surface area, disrupt flow and induce turbulence. Thus increasing the mix between the gas and the viscoelastic fluid.

Specific values of the injection pressures $P_0$ and $P_1$ have an effect in the concentration of bubbles in foam 410 and their size distribution. For example, while $P_{out}$ is typically 1 atm (atmosphere), $P_0$ may be 1.2 atm or 1.5 atm. Also, $P_1$ is slightly lower than $P_0$, in order to force the gas to mix with the viscoelastic liquid. For example, if $P_0$ is 1.2 atm, $P_1$ is selected to be about 1.1 atm; while for $P_0$=1.5 atm, $P_1$ may be selected as 1.2 atm. Other values for $P_{out}$, $P_0$, and $P_1$ may be used in embodiments consistent with FIG. 5, resulting in viscoelastic foam 410 having slightly different properties. The dimensions of dual chamber injector 420, and nozzle 425 may be adjusted as well to produce the desired combination of bubble radii and inter-bubble distances. The Young Modulus of the viscoelastic material may also affect bubble radii. In the example discussed above, viscoelastic foam 410 has bubbles ranging in size from a few hundredths of nanometers in diameter (100-200 nm) up to several microns (2-5 μm). In such case, a mean bubble size of about 1 μm may be obtained.

In some embodiments consistent with FIG. 5, gas reservoir 510 may be the atmosphere, and thus $P_0$ may be close to or about atmospheric pressure. The viscoelastic fluid may then be injected at a pressure $P_1$, generating a Venturi effect in nozzle 425 by which filtered air would be drawn into and mixed with the viscoelastic fluid. A Venturi effect in nozzle 425 results in the acceleration of the fluid flow due to the constriction of the flow cross-section. This acceleration is prompted by a drop in $P_{out}$, which in turn induces a suction effect at gas reservoir 510, drawing gas to mix with the viscoelastic fluid.

While some embodiments use air as the gas for bubbles in material 410, other gases may be consistent with the embodiments described herein. For example, inert gases such as Ar, or Xe may also be used. Gases such as $N_2$ or $CO_2$ may be employed as well.

In some embodiments consistent with FIG. 5, it may be desired to provide a highly purified gas in reservoir 510 to form the bubbles. Exogenous particles may contaminate TM 100 or JCT 110, blocking the pores in the tissue. These particles may be removed from the gas prior to mixing with a viscoelastic material to form foam 410. Furthermore, chemical or biological contaminants may be removed from the gas in order to avoid infection or scarring of TM 100 or JCT 100. Also, contaminants that may provide absorption centers for laser beam 170 may be removed from the gas and viscoelastic material in foam 410. A light absorbing particulate embedded in material 410 may produce burning and further contamination of material 410 and surrounding tissue. Burning material may undesirably deplete laser beam fluence 251 much before it reaches its target. To avoid contamination, injector 420 may include filter 515 between reservoir 510 and nozzle 425. Filter 515 may be a filtering media having chemical or physical affinity for certain contaminants or particulates.

Figure 6:
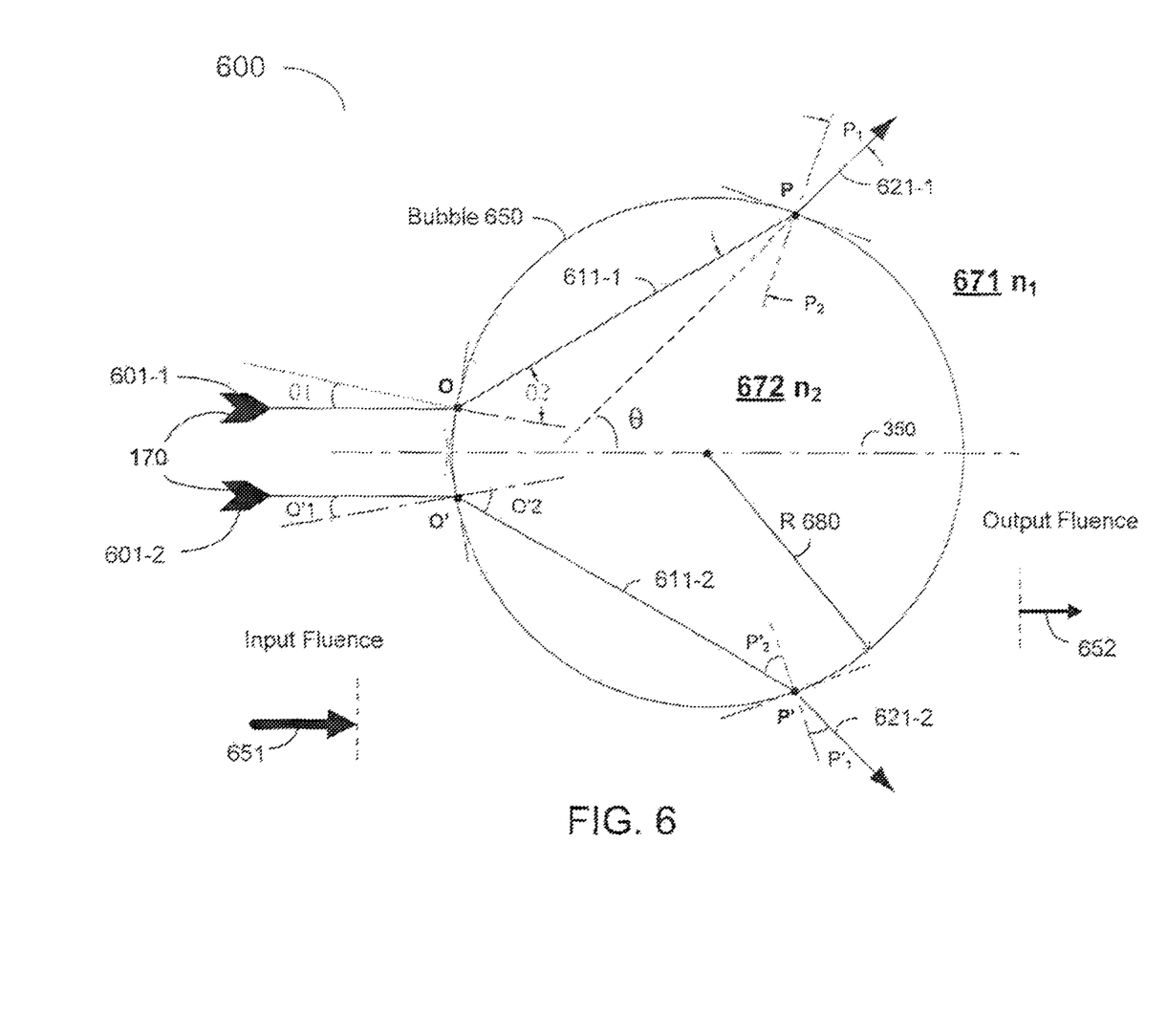
FIG. 6 shows a light beam including rays impinging on a bubble having an index of refraction different from that of the surrounding medium, according to some embodiments.

FIG. 6 shows light beam 170 including rays 601-1 and 601-2 impinging on bubble 650, having radius 680 (R). Bubble 650 may be one of a multiplicity of bubbles included in foam 410. Bubble 650 may contain a gas with index of refraction 672 ($n_2$), different from that of the surrounding medium 671 ($n_1$). The surrounding medium may be a viscoelastic material such as used to form material 410 (cf. FIG. 4 above). According to some embodiments consistent with FIG. 6, index 672 may have a lower value than index 671. Furthermore, R 680 may be larger than the light wavelength in beam 170. In some embodiments, R 680 may be a few times larger than 2, or even orders of magnitude larger. More specifically, some embodiments may have R 680 larger than the value of $\lambda/n_2$, where $\lambda$ is the wavelength of light used in beam 170.

Ray 601-1 impinging on bubble 650 at point O forms angle $O_1$ with the normal to the bubble's surface at that point. Due to a change in index of refraction from $n_1$ 671 to $n_2$ 672, ray 601-1 may be deflected into ray 611-1, forming angle $O_2$ with the normal. The relation between angles $O_1$ and $O_2$ is given by Snell's law of refraction. As a rule of thumb, for $n_2<n_1$, then $O_2>O_1$ and ray 611-1 may be directed away from beam path 250. Ray 611-1 travels through bubble 650 forming a straight path, and exits bubble 650 at point P. At point P, the transition from refractive index $n_1$ 671 to $n_2$ 672 may deflect ray 611-1 into ray 621-1. Ray 611-1 forms angle $P_2$ with the normal to bubble 650 at point P, and ray 621-1 forms angle $P_1$. Similarly to what happens at point O, for $n_2<n_1$, then $P_2>P_1$. Thus, ray 621-1 is deflected further away from beam path 250, forming a net angle 'θ' with path 250. A similar occurrence takes place for ray 601-2 in beam 170. As ray 601-2 goes through bubble 650, it is deflected into rays 611-2 and 621-2 at points O' and P', respectively. According to the same physical phenomenon described above for ray 601-1, $O'_1<O'_2$, and $P'_1<P'_2$. Thus, beam 621-2 is also deflected away from beam path 250.

From the above description, it is seen that input fluence 651 is higher than output fluence 652 as beam 170 goes through bubble 650. This is at least because of the increase in beam cross section, since all rays in the beam are pushed away from beam path 250. Also, the spreading of the rays in directions fanning away from path 250 reduces the fluence of each ray in beam 170 in the direction of path 250 by at least the Cosine of angle θ. Moreover, there is a net energy loss for each ray 601-1 and 601-2 at interface points O, O', P and P' due to indexes 671 and 672 being different: $n_1 \neq n_2$. According to electromagnetic field theory, a difference in refractive index leads to a non-zero component of the electric field in the direction normal to the bubble's surface at each interface point. This non-zero field component creates a dipole polarization of the materials on either side of the interface. Dipole creation extracts energy away from the radiant energy of the electromagnetic field. This energy may be dissipated via different mechanisms, for example the heating of the material as the molecules are displaced against viscoelastic forces in order to form the polarization field.

The reduction in fluence of beam 170 illustrated in FIG. 6 for one bubble may be multiplied for each bubble encountered by beam 170 along path 250 in the presence of material 410. In some embodiments, the net effect of this multiplicative process may be rays 621 deflected away from path 250 at many different angles θ, such as 90° or more. The scattering power of a multiplicity of bubbles 650 forming viscoelastic foam 410 may be measured as the loss in beam fluence along path 250. Thus, a larger scattering power may be associated with a higher fluence loss for beam 170, and a lower scattering power may be associated with a lower fluence loss.

Some factors that may affect the scattering power of viscoelastic foam 410 may be the relative difference in value of indexes 671 and 672. In some embodiments an increase in the difference between 671 and 672 may increase the scattering power. One factor that may also affect the scattering power of viscoelastic foam 410 is the light wavelength, $\lambda$, of beam 170. A smaller value of $\lambda$ may increase the scattering power, while a larger value of $\lambda$ may reduce the scattering power. Other factors that may affect the scattering power of foam 410 are the radius 680 of bubbles 650, and their relative distance from one another. According to embodiments consistent with FIG. 6, a larger radius 680 may have the effect of increasing the scattering power. Also, a shorter relative distance between bubbles 650 in foam 410 may have the effect of increasing the scattering power. To the contrary, a shorter radius 680 may reduce the scattering power. And a longer relative distance between bubbles 650 in foam 410 may also reduce the scattering power.

While indexes 671 and 672 may be selected by a choice of materials composing foam 410, wavelength λ may be selected by choosing the laser for beam 170. In some embodiments, wavelength λ may be selected by using an optical filter or some tuning device well known in the art. Radius R 680 and the relative distance between bubbles in foam 410 may be selected by adjusting flow dynamical parameters in injector 420. This has been discussed in detail above in relation to FIG. 5.

In some embodiments, bubbles 650 embedded in foam 410 may have a distribution of sizes, rather than all or mostly all bubbles having the same radius R 680. The distribution of bubble sizes in foam 410 may follow a number of different statistical models, having a mean value R 680 and a variance around the mean, ΔR. The mean value R 680, and variance, ΔR, may be affected by parameters as described above: gas pressure, dynamic properties of nozzle, or Young Modulus of the viscoelastic material.

Figure 7:
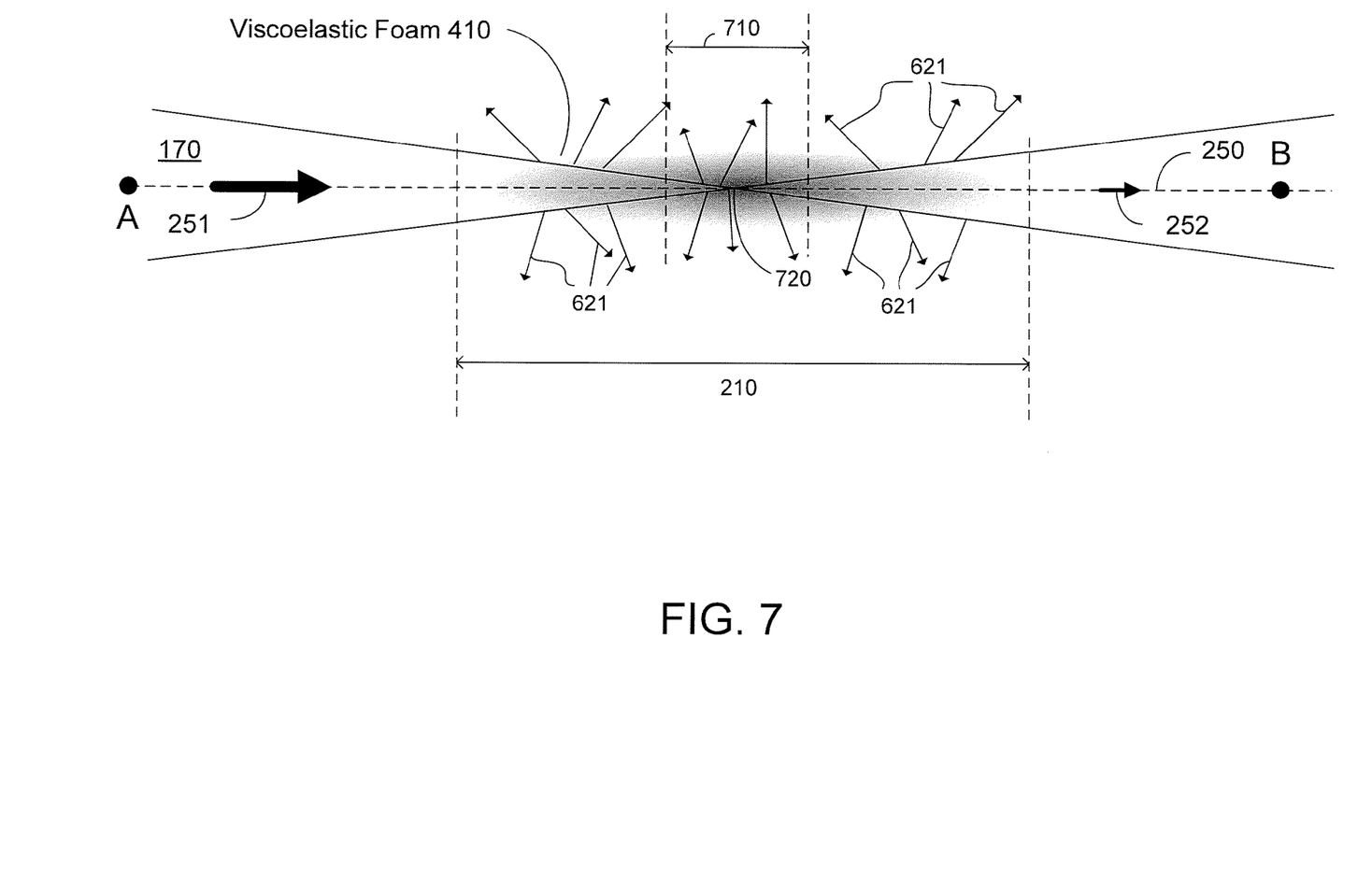
FIG. 7 shows a light beam having an input fluence converging to a focal point along a beam path in the presence of a viscoelastic foam, according to some embodiments.

FIG. 7 shows light beam 170 having input fluence 251 converging to focal point 720, according to beam path 250. The focusing of beam 170 creates effective fluence portion 710 in the presence of viscoelastic foam 410, according to some embodiments. Also illustrated for comparison in FIG. 7 is effective fluence portion 210. As described above in relation to FIG. 2, portion 210 may correspond to beam 170 having input fluence 251 and beam path 250 in the absence of viscoelastic foam 410. The presence of bubbles 650 in foam 410 induce scattering processes as described above in relation to FIG. 6. Thus, rays 621 are scattered off beam path 250 at different angles, depleting input fluence 251 in beam 170 to result in output fluence 252, much reduced. According to embodiments consistent with FIG. 7, portion 710 may be shorter than portion 210, as will be described in relation to FIG. 8, below.

Figure 8:
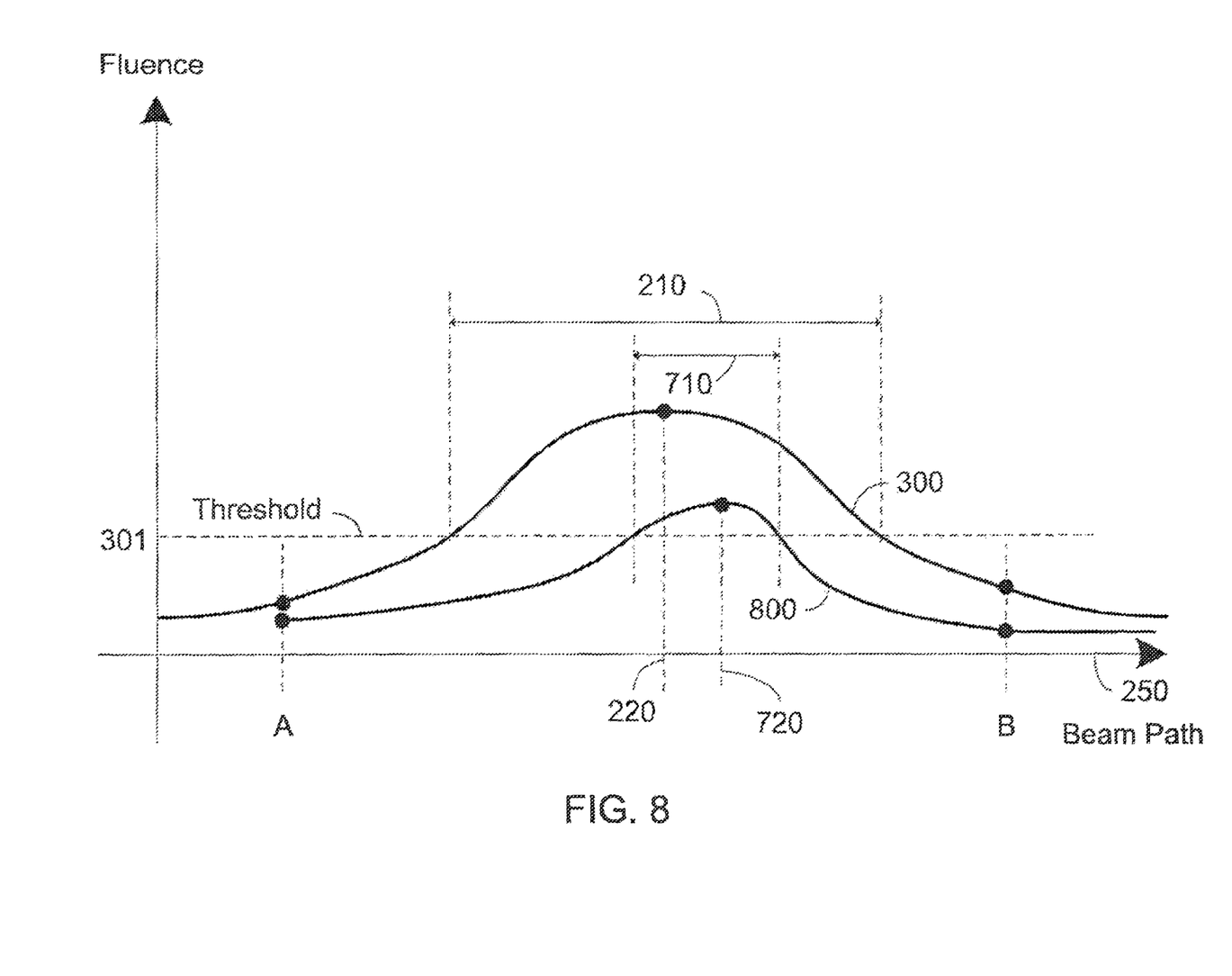
FIG. 8 shows a curve of the fluence of a laser along a beam path having a focal point, in the presence of a viscoelastic foam, according to some embodiments.

FIG. 8 shows curve 800 of fluence 251 for beam 170 along path 250 having focal point 720, in the presence of viscoelastic foam 410, according to some embodiments By comparison, curve 300 (cf. FIG. 3) for a configuration in the absence of foam 410, is overlaid to curve 800 in FIG. 8. Fluence threshold ψ 301 may be the same with and without foam 410. For example, in embodiments where ψ 301 is the fluence ablation threshold of TM 100 or JCT 110, the value may not be affected by the presence/absence of foam 410. This is because a cell may respond to the influx of energy regardless of the chemical or physical conditions of its surroundings. Some tissues in different parts of the body may in fact have a different behavior.

As illustrated in FIG. 8, the effect of placing foam 410 along beam path 250 may be to reduce the effective fluence portion of path 250 from portion 210 to portion 710. The reason for this is the depletion of input fluence 251 from beam 170 produced by the scattering power in foam 410, as described in relation to FIG. 6, above. It is seen from FIG. 8 that the effect of the scattering power in foam 410 is to reduce fluence 251 from curve 300 to curve 800 at points along path 250. In some embodiments, while curve 300 may be symmetric with respect to focus 220, curve 800 may not be symmetric with respect to focus 720. The presence of foam 410 may place focus 720 at a different place along path 250 relative to point 220. This may occur in a situation where the scattering power of foam 410 and tissue TM 100 may not be homogeneous along beam path 250. For example, a higher scattering power along points located between point A and focus 220 may displace point 720 closer to point B. Such a situation may be consistent with the embodiment depicted in FIG. 8. Moreover, the opposite situation may occur: greater scattering power in the portion between point 220 and point B. Then, focus 720 may be displaced closer to point A relative to point 220.

Notwithstanding the detailed shape of curve 800, embodiments having foam 410 along path 250 may increase fluence dissipation for beam 170. This has the effect of pushing curve 300 down to curve 800 in the presence of energy-dissipating material 410. Since fluence threshold 301 remains the same or similar to a situation with no material 410, the result is shrinking of effective fluence portion from portion 210 to portion 710. The shrinkage of 210 to portion 710 means that foam 410 may provide a higher spatial resolution to TM 100 and JCT 110 ablation, as mentioned above in relation to FIG. 4.

In the embodiments described above in relation to FIGS. 2 and 7, beam 170 converges to a single point at focus 220 and 720. This is a schematic representation that may not conform to some embodiments. In general, laser beam 170 presents a finite waist '$\omega_o$' at focal point 220. For an optical system that forms beam 170, there may be a limit to the degree of focusing achieved. This limit may be given by diffraction properties of electromagnetic waves. For example, for a lens having focal length f and diameter, D, a beam waist '$\omega_o$' in a medium with refractive index, n, at wavelength, λ, may be given by:

$$\omega_o = 1.22 \cdot \lambda \cdot \frac{f}{nD} \quad (1)$$

Equation (1) represents a minimum value for beam waist '$\omega_o$.' Some embodiments may have a beam waist '$\omega_o$' larger than what is obtained from Eq. (1). The finite dimension of beam 170 in the direction perpendicular to path 250 provides a transversal resolution for tissue ablation procedure 400. As expressed by Eq. (1), the resolution may be proportional to the light wavelength, λ, in beam 170. Furthermore, fluence threshold 301 may also affect the transversal resolution of procedure 400, as will be described in detail in relation to FIG. 9, below.

Figure 9:
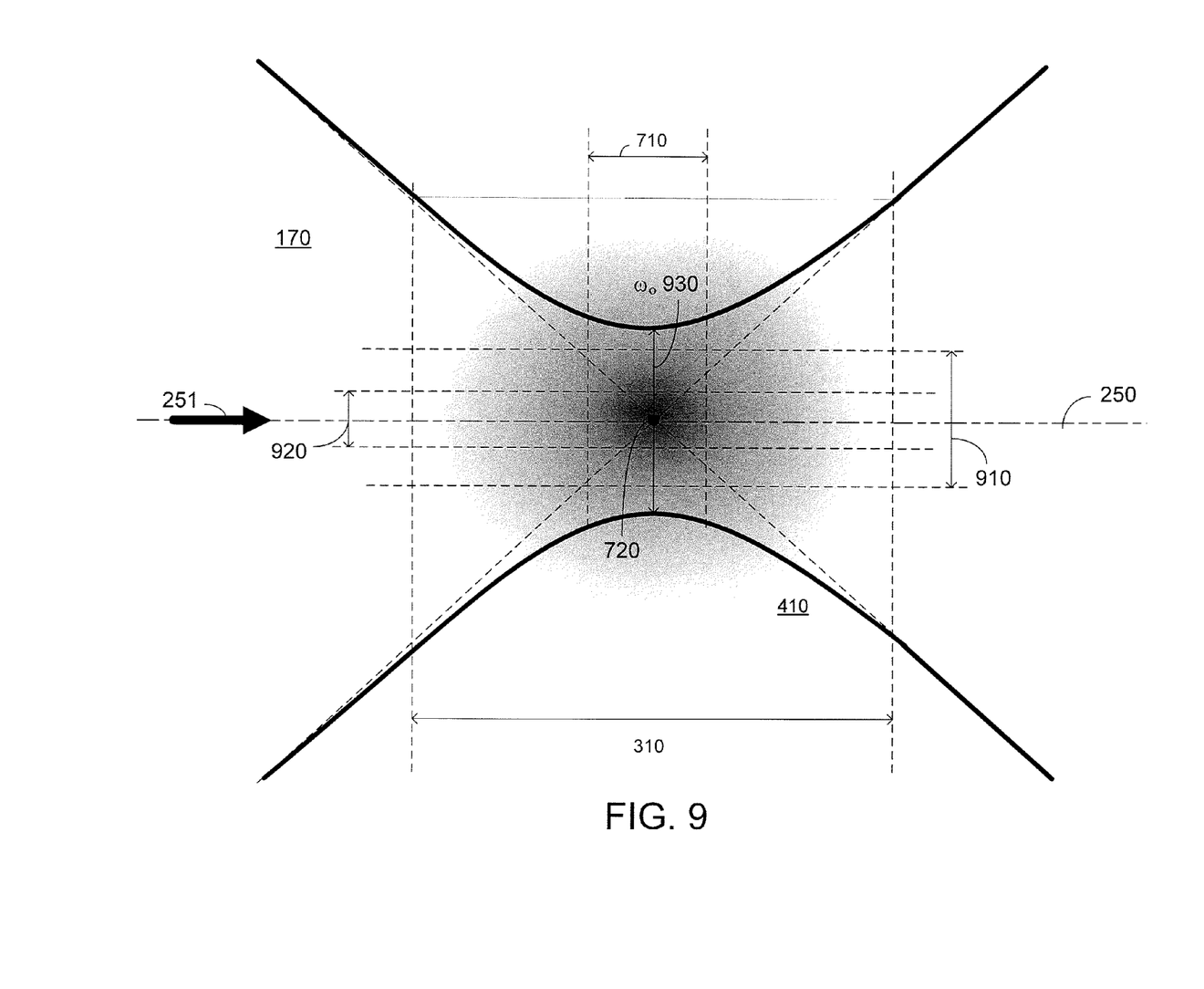
FIG. 9 shows a light beam having an input fluence converging to a focal point according to a beam path in the presence of a viscoelastic foam, according to some embodiments.

FIG. 9 shows light beam 170 having fluence 251 converging to focal point 720 along beam path 250 in the presence of material 410, according to some embodiments. Consistent with the above discussion, the embodiment illustrated in FIG. 9 may also include beam waist '$\omega_o$' 930 at focal point 720. In the absence of foam 410, a transversal resolution 910 may be determined by a transversal portion of beam 170 having fluence values higher than threshold ψ 301. It has been shown that effective fluence portion 210 is shrunk to portion 710 in the presence of material 410. Likewise, transversal resolution 910 may be reduced to a value 920 in the presence of foam 410, as illustrated in FIG. 9. The presence of material 410 having a scattering power induces energy dissipation of beam 170 along path 250 and also along a transversal dimension. This reduces the fluence in beam 170 at every point along the transversal direction, shrinking the transversal resolution accordingly.

FIG. 9 shows beam 170 having a symmetric profile about point 720. Some embodiments consistent with the general features of FIG. 9 may include a beam 170 that is not symmetric relative to point 720. This may be the case for an inhomogeneous distribution of material 410 along path 250. Moreover, according to embodiments consistent with FIG. 9, the profile of beam 170 may not be axially symmetric about path 250. Regardless of the detailed shape of beam 170, the shrinkage of effective fluence portions 210 and 910 to portions 710 and 920 results from presence of material 410.

Thus, it is seen that according to embodiments such as illustrated in FIG. 4, laser-based surgical technique 400 including energy-dissipating material 410 may provide a high resolution for tissue ablation in every spatial direction.

Figure 10:
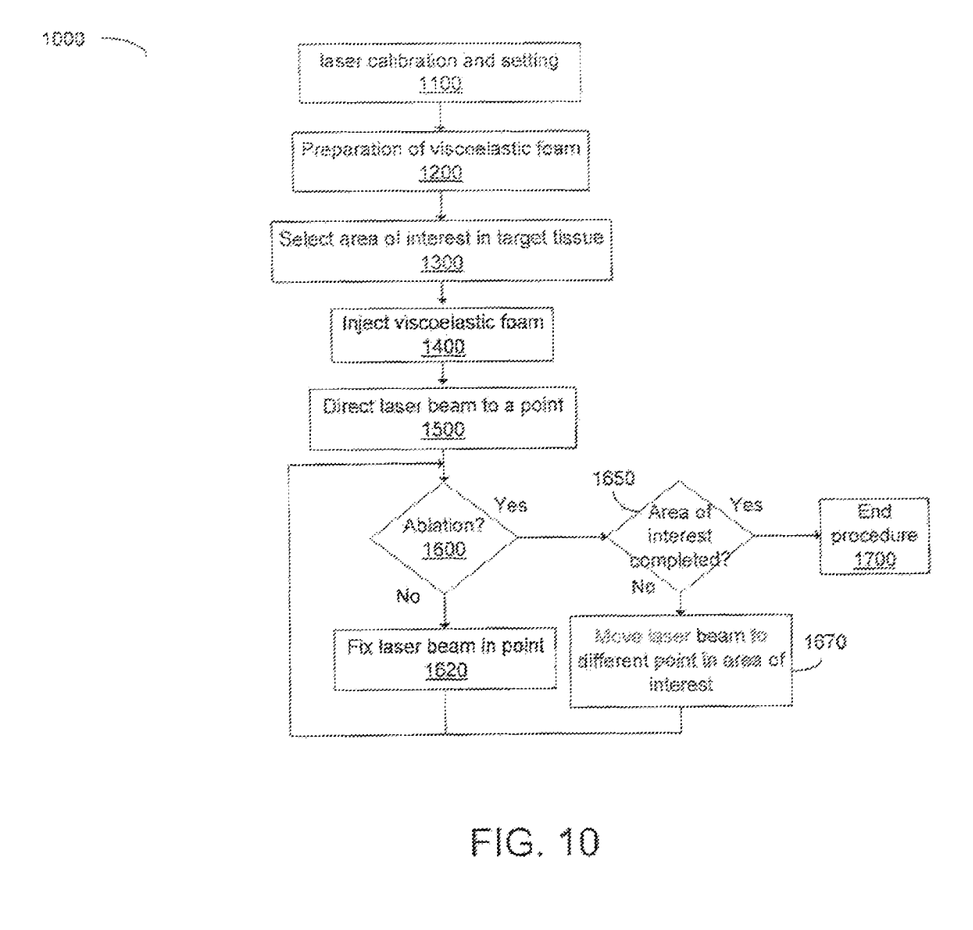
FIG. 10 shows a flow diagram for a method to perform a light beam ablation procedure in the Trabecular Meshwork as in FIG. 4, according to some embodiments.

FIG. 10 shows a flow diagram for method 1000 to perform a light beam ablation procedure in the Trabecular Meshwork as in FIG. 4, according to some embodiments. In step 1100 laser beam 170 is setup and calibrated for operation. The setup may include the steps of aligning optical components in order to collimate beam 170 and then focus it to a point in an area of interest. The calibration of beam 170 may include the steps of measuring and setting the wavelength of beam 170. Calibration of beam 170 may further include the steps of setting the power level of the beam to the appropriate value for the tissue being targeted. Further, calibration of the beam may include setting the pulse repetition rate, $\Omega$, and the pulse duration, $\tau$, when laser beam 170 is used as a pulsed beam. In this manner, calibration of laser beam 170 may set input fluence 251 for the procedure according to pre-selected values. For example, input fluence 251 may be set slightly above a fluence ablation threshold appropriate for TM 100 or JCT 110.

In step 1200 highly dissipative material 410 may be prepared according to pre-selected conditions. Material 410 may be a viscoelastic foam as described above. Step 1200 may include selecting the pressure at which a gas will be combined with a viscoelastic material, or the rate of injection. Step 1200 may also include purifying the gas in order to remove any contaminants that may be present. Gas purification may be accomplished by passing the gas through a series of filters having predetermined porosity so that any sizeable particulates may be trapped in the filter. Furthermore, the filters used to purify the gas may include certain chemicals and solvents having affinity to particulates, chemicals and bio-agents that may be present in the gas. Step 1200 may also include the step of setting the flow-dynamic conditions in injector 420. For example, injector 420 may be adjusted to provide a mix of viscoelastic material and gas bubbles having a size distribution to enhance the scattering power of viscoelastic foam 410.

In step 1300 a user selects an area of interest in the target tissue, for ablation. In some embodiments, a user may select a portion of TM 100 or JCT 110 from region 102, based on visual inspection of the tissue. For example, a portion of TM 100 or JCT 110 blocking the flow of aqueous humor to SC 150 may be identified using a high magnification microscope. In some embodiments of method 1000 a target tissue may be a scarred protrusion in TM 100 or JCT 110. Also, a target tissue may be scar tissue in portions of IW 157 or OW 159. Some examples of target tissue may include swollen portions of TM 100 or JCT 110 that may be the result of an infectious process.

In step 1400 injector 420 is used to place material 410 in the area of interest. For example, material 410 may be placed in area 102 (cf. FIG. 1) including JCT 110 tissue and SC 150. In some embodiments of method 1000, step 1400 may include filling SC 150 in area 102 with material 410. By filling SC 150 with material 410, a separation may be provided between IW 157 and OW 159, avoiding collapse of SC 150. Thus, ablation damage by laser beam 170 beyond TM 100 and JCT 110 may be prevented. In step 1400, some embodiments may further provide colored dye 430 to enhance visual contrast in the area of interest. For example, colored dye 430 may have affinity for a specific tissue, such as TM 100 and JCT 110, and not for SC 150. Thus, dye 430 may indicate to a user the target tissue for procedure 400. In some embodiments colored dye would increase the contrast ratio of SC 150 allowing it to be seen through TM 100 and JCT 110 for eyes having light pigmentation. Thus allowing the user to target the appropriate area of TM 100 and JCT 110 for ablation. In some embodiments colored dye 430 may also be a fluorescent material that may be excited by laser beam 170. Thus, when laser beam 170 scans the area of interest in TM 100 or TM 110, a glowing spot may indicate a user performing method 1000 the exact location of laser beam 170.

In step 1500 laser beam 170 is directed to a point in the area of interest. To perform step 1500, a suitable optical system may be used including at least a mirror and a lens or an endoscope. An optical system used to perform step 1500 may also include at least one optical fiber to transport beam 170 for a portion of its trajectory. In some embodiments, the optical fiber may have a tapered tip with a lens in the distal end. The distal end of the optical fiber is the end closer to the target tissue. In some embodiments, the optical system may also include a gonioscope and a microscope. A microscope providing optical magnification may be used to visualize area 102 where the target tissue may be located, with material 410 covering the area of interest.

In step 1600 a determination is made whether or not tissue ablation has occurred at the desired point. In some embodiments, step 1600 may be performed by visual inspection through a microscope. In some embodiments, a sensor may be included in step 1600 to indicate tissue ablation. For example, a sensor may be used to detect the presence of gas bubbles produced by the vaporization of tissue components. Some embodiments may also include a hemoglobin sensor to perform step 1600. A hemoglobin sensor may detect the presence of blood in ablated tissue as capillary vessels may be ruptured in process 400.

If ablation is not reached, in step 1620 beam 170 is fixed at the point of interest, until ablation is achieved. Furthermore, in some embodiments step 1620 may include the adjustment of certain parameters in the system in order to attain ablation. For example, fluence 251 may be increased until ablation is obtained. In some embodiments, an optical component may be used to adjust beam path 250 in order to increase fluence 251. For example, focal point 720 may be displaced between points A and B along beam path 250 to increase fluence 251 at the point of interest. Furthermore, in some embodiments an optical component may be adjusted so that beam waist '$\omega_o$' 930 is reduced and fluence 251 increased. Fluence 251 of beam 170 may be increased simply by adjusting parameters in the calibration and setup of beam 170. For example, the power of the laser may be increased. In some embodiments using a pulsed beam 170, fluence 251 may be raised by increasing the pulse rate. Furthermore, fluence 251 may be increased by reducing pulse duration, while maintaining the average laser power constant.

If ablation is detected in step 1600, in step 1650 an assessment is made whether or not ablation in the area of interest has been completed. Step 1650 may be performed by the user with a high magnification microscope. By looking at a magnified view of area 102 covering the area of interest, the user may establish if the blocking tissue in TM 100 or JCT 110 has been removed. If ablation in the area of interest has been completed, procedure 400 is finished and method 1000 ends in step 1700. If ablation in the area of interest is not completed, in step 1670 laser beam 170 is moved to a different point. Thus, method 1000 is repeated from step 1600. Step 1670 may be performed by using a gonioscope including a mirror, or an endoscope. In some embodiments, step 1670 may include the reduction of fluence 251 while beam 170 is moved across the area of interest. Fluence 251 may be reduced below the fluence ablation threshold for TM 100 or JCT 110 in step 1670. In some embodiments, fluence 251 may be reduced much lower than ablation threshold of TM 100, JCT 110, and any other surrounding tissue, in step 1670. Laser beam 170 may not be completely turned off in step 1670 so that the controller is able to visualize the laser spot in the target tissue. Reducing fluence 251 of beam 170 while it is moved from point X to point Y may prevent undesired damage in the intervening tissue. In some embodiments, beam 170 may be turned off altogether in step 1670, while a soft illumination source provides lighting for viewing the area of interest. Once step 1670 is completed, method 1000 is repeated from step 1600.

The steps described above to perform method 1000 may be provided for surgical procedures other than laser-based trabeculectomy. For example, surgical procedures for the treatment of glaucoma may be carried out using method 1000. In general, some embodiments may include the use of method 1000 for surgical procedures in ophthalmology, including parts of the eye such as Retina 90, Cornea 20, Iris 40, or Ciliary Body 70 (cf. FIG. 1). Moreover, other laser-based surgical procedures for different parts of the body may be envisioned using method 1000 to enhance the resolution of laser ablation.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. A method of performing high resolution tissue ablation in the eye, the method comprising:
    forming a beam to provide optical energy;
    providing a viscoelastic foam;
    placing the viscoelastic foam adjacent to a trabecular meshwork of an eye and in Schlemm's canal of the eye; and
    after the viscoelastic foam is placed, directing the beam to the trabecular meshwork.

2. The method of claim 1 wherein providing the viscoelastic foam comprises the steps of:
    selecting a viscoelastic material having a first index of refraction; and
    forming a multiplicity of gas bubbles in the viscoelastic material, the gas bubbles having a second index of refraction.

3. The method of claim 2 wherein the optical energy is laser light having a wavelength.

4. The method of claim 1 including the step of placing a color dye adjacent to the trabecular meshwork together with the high energy dissipating material.

5. The method of claim 4 wherein placing the color dye and the energy dissipating material comprises the use of an injector.

6. The method of claim 5 wherein forming the beam to provide optical energy is performed in the injector.

7. The method of claim 1 wherein forming the beam to provide optical energy comprises the use of a gonioscope.

8. The method of claim 1 wherein forming the beam to provide optical energy comprises the use of an optical fiber.

9. The method of claim 8 wherein the optical fiber has a tapered tip forming a lens in the distal end.

\* \* \* \* \*